United States Patent [19]
Maignan et al.

[11] Patent Number: 4,829,080
[45] Date of Patent: May 9, 1989

[54] AROMATIC BENZOPYRANYL AND BENZOPYRANYL COMPOUNDS; THEIR PREPARATION; AND THEIR USE IN COSMETIC COMPOSITIONS AND HUMAN AND VETERINARY MEDICINE

[75] Inventors: Jean Maignan, Tremblay-les-Gonesse; Gérard Lang, Saint-Gratien; Gérard Malle, Villers sur Morin; Serge Restle, Aulnay Sous Bois; Braham Shroot, Antibes, all of France

[73] Assignee: L'Oreal, Paris, France

[21] Appl. No.: 25,200

[22] Filed: Mar. 12, 1987

[30] Foreign Application Priority Data

Mar. 12, 1986 [LU] Luxembourg ............................ 86351

[51] Int. Cl.$^4$ .................... A61K 31/35; A61K 31/38; C07D 311/58; C07D 335/06
[52] U.S. Cl. .................................. 514/432; 514/456; 514/457; 549/23; 549/399; 549/400; 549/404; 549/405; 549/407; 549/408
[58] Field of Search .................. 549/23, 399, 400, 404, 549/405, 407, 408; 514/432, 456, 457

[56] References Cited
FOREIGN PATENT DOCUMENTS
2119801 11/1983 United Kingdom ................... 549/23

OTHER PUBLICATIONS
Chemical Abstracts, vol. 104, 1986, p. 696, No. 129843x, Dauksas et al.

Primary Examiner—Mary C. Lee
Assistant Examiner—MarySue Howard
Attorney, Agent, or Firm—Cushman, Darby & Cushman

[57] ABSTRACT

An aromatic benzopyranyl or benzothiopyranyl compound of the formula wherein
n is 0 or 1,
X represents $-O-$, $-S-$, $-S-$ or $-S-$
                ↓       ↓↘
                O      O  O R' represents H, OH, acyloxy or NH$_2$,
R" represents H or alkoxy or
R' and R" taken together form an oxo, methano or hydroxyimino radical,
R$_8$ represents H, $-OR_9$ or $-N'\genfrac{}{}{0pt}{}{r'}{r''}$, R$_9$ represents H, alkyl, mono or polyhydroxyalkyl, aryl, aralkyl, a residue of a sugar or $-(CH_2)_p-N'\genfrac{}{}{0pt}{}{r'}{r''}$, p equals 1, 2 or 3,
r' and r" represent H, alkyl, monohydroxyalkyl, polyhydroxyalkyl, aryl, benzyl, the residue of an amino acid or an aminated sugar, or together form a heterocycle,
R$_1$, R$_2$, R$_3$ and R$_4$ represents H or lower alkyl,
R$_5$, R$_6$ and R$_7$ represent H or methyl or when n=1, R$_5$ and R$_7$ taken together form with the benzene ring a naphthalene ring (R$_5$-R$_7$=—CH=CH—), and
the salts of said compounds as well as their geometric and optical isomers.

These compounds are useful in pharmaceutical and cosmetic compositions.

11 Claims, No Drawings

AROMATIC BENZOPYRANYL AND BENZOPYRANYL COMPOUNDS; THEIR PREPARATION; AND THEIR USE IN COSMETIC COMPOSITIONS AND HUMAN AND VETERINARY MEDICINE

BACKGROUND OF THE INVENTION

The present invention relates to new aromatic benzopyranyl and benzothiopyranyl compounds, to a process for their preparation and to their use in human or veterinary medicine and in cosmetic compositions.

These new compounds are usefully employed in the topical and systemic treatment of dermatologic diseases linked to a keratinization disorder (differentiation—proliferation) and dermatologic diseases (or others) having inflammatory and/or immunoallergic components and in the treatment of illnesses of the degeneration of conjunctive tissue. They also exhibit anti-tumor activity.

Moreover, these compounds can be employed in the treatment of atrophy, be it cutaneous or respiratory, and in the treatment of rheumatoid psoriasis.

These compounds also possess good activity against the germs involved in acne.

Finally, the compounds of the present invention are usefully employed in the opthamology field and principally in the treatment of corneopathies.

The aromatic benzopyranyl and benzothiopyranyl compounds of the present invention can be represented by the formula;

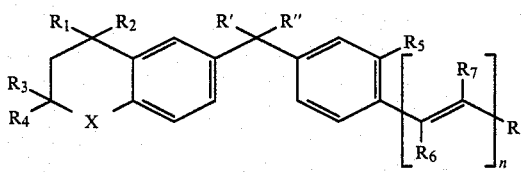

wherein,
n is 0 or 1,
X represents

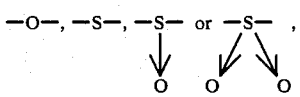

R' represents hydrogen, OH, alkoxy having 1-4 carbon atoms, acyloxy having 1-4 carbon atoms, or $NH_2$, R" represents hydrogen, or alkoxy having 1-4 carbon atoms, or R' and R" together form an oxo radical (=O), a methano radical (=$CH_2$) or a hydroxyimino radical (=N—OH), R represents —$CH_2OH$ or —$COR_8$,
$R_8$ represents hydrogen, —$OR_9$ or 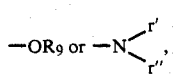

$R_9$ represents hydrogen, linear or branched alkyl having 1-20 carbon atoms, mono or polyhydroxyalkyl, aryl or aralkyl optionally substituted, or the residue of a sugar or even the radical

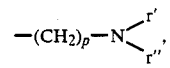

p is 1, 2, or 3, r" and r" each independently represent hydrogen, loweralkyl, monohydroxyalkyl optionally interrupted by a heteroatom, or polyhydroxyalkyl, aryl or benzyl optionally substituted, the residue of an aminoacid or an aminated sugar, or together form a heterocycle, $R_1$, $R_2$, $R_3$ and $R_4$ each independently represent hydrogen or lower alkyl, $R_5$, $R_6$ and $R_7$ represent hydrogen or methyl, or when n=1, $R_5$ and $R_7$, taken together, form with the benzene ring a naphthalene ring ($R_5$-$R_7$=—CH=CH—), and the salts of said compounds of formula I as well as their geometric and optical isomers.

By lower alkyl radical is meant an alkyl radical having 1-6 carbon atoms and principally methyl, ethyl, isopropyl, butyl and tert.butyl.

By monohydroxyalkyl is meant a radical having 2-6 carbon atoms and principally 2-hydroxy ethyl, 2-hydroxy propyl or 2-hydroxy ethoxyethyl.

By polyhydroxyalkyl is meant a radical containing 3-6 carbon atoms and 2-5 hydroxy groups such as 2,3-dihydroxy propyl, 1,3-dihydroxy propyl or the residue of pentaerythritol.

By aryl is meant phenyl optionally substituted by halogen, hydroxy, nitro, lower alkyl, —$CF_3$ or —COOH.

By residue of an aminoacid is meant a residue derived, for example, from α- or β-alanine or from methionine.

By residue of a sugar is meant a residue derived from, for example, glucose, mannose, erythrose or galactose.

By residue of an aminated sugar is meant a residue derived, for example, from glucosamine, galactosamine or mannosamine.

When the radicals r' and r" taken together form a heterocycle, the heterocycle is, preferably, piperidino, piperazino, morpholino, pyrrolidino or 4-(2-hydroxyethyl) piperazino.

When the compounds according to the present invention are provided in the form of salts, they can be salts of an alkali or alkaline earth metal or even of zinc, or of an organic amine when they carry at least one free acid function, or of salts of a mineral or organic acid, principally the hydrochloride, hydrobromide or citrate when they carry at least one amine function.

The preferred compounds of the present invention are those responding to formulas II and III below:

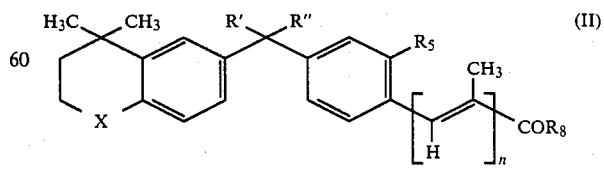

wherein
n is 0 or 1,
X is

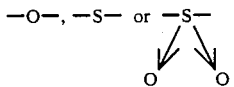

R' and R" taken together form an oxo radical, or R' represents hydroxyl and R" represents hydrogen, $R_8$ represents

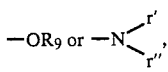

$R_9$ represents hydrogen or lower alkyl,
r' represents hydrogen, and
r" represents lower alkyl or a mono or polyhydroxyalkyl; and

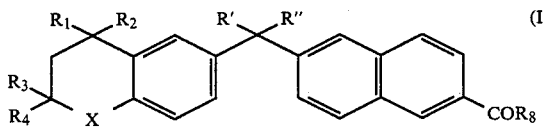

wherein

X represents —O— or —S—,

R' and R" taken together form an oxo radical, or R' represents hydrogen or hydroxyl and R" represents hydrogen, $R_1$ and $R_2$ each identically represent (i) methyl and in this case $R_3$ and $R_4$ represent hydrogen, or (ii) hydrogen, and in this case $R_3$ and $R_4$ represent methyl, $R_8$ represents hydrogen,

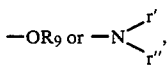

$R_9$ represents hydrogen or lower alkyl,
r' represents hydrogen, and
r" represents lower alkyl or a mono or polyhydroxyalkyl radical.

The particularly preferred compounds of formula III above are those in which $R_1$ and $R_2$, identically represent methyl and $R_3$ and $R_4$ represent hydrogen.

Representative compounds of formula I, above, include the following:

(1) 4-(4,4-dimethyl-3,4-dihydro-6-benzopyranyl) carbonyl methyl benzoate,
(2) 4-(4,4-dimethyl-3,4-dihydro-6-carbonyl benzoic acid,
(3) N-ethyl-4-(4,4-dimethyl-3,4-dihydro-6-benzopyranyl) carbonyl benzamide,
(4) 4-(4,4-dimethyl-3,4-dihydro-6-benzothiopyranyl) carbonyl methyl benzoate,
(5) 4-(4,4-dimethyl-3,4-dihydro-6-benzothiopyranyl) carbonyl benzoic acid,
(6) 4-(4,4-dimethyl-3,4-dihydro-1,1-dioxide-6-benzothiopyranyl) carbonyl benzoic acid,
(7) 6-(4,4-dimethyl-3,4-dihydro-6-benzothicpyranyl) carbonyl 2-methyl naphthalene carboxylate,
(8) 6-(4,4-dimethyl-3,4-dihydro-6-benzothopyranyl) carbonyl 2-naphthalene carboxylic acid,
(9) N-ethyl-6-(4,4-dimethyl-3,4-dihydro-6-benzothiopyranyl) carbonyl 2-naphthalene carboxamide,
(10) 6-(2,2-dimethyl-3,4-dihydro-6-benzopyranyl) carbonyl 2-methyl naphthalene carboxylate,
(11) 6-(4,4-dimethyl-3,4-dihydro-6-benzopyranyl) carbonyl 2-methyl naphthalene carboxylate,
(12) 6-(2,2-dimethyl-3,4-dihydro-6-benzopyranyl) carbonyl 2-naphthalene carboxylic acid,
(13) 6-(4,4-dimethyl-3,4-dihydro-6-benzopyranyl) carbonyl 2-naphthalene carboxylic acid,
(14) N-ethyl-6-(4,4-dimethyl-3,4-dihydro-6-benzopyranyl) carbonyl 2-naphthalene carboxamide,
(15) N-ethyl-6-(4,4-dimethyl-3,4-dihydro-6-benzopyranyl) hydroxymethyl 2-naphthalene carboxamide,
(16) 6-(4,4-dimethyl-3,4-dihydro-6-benzopyranyl) hydroxymethyl 2-naphthalene carbinol,
(17) 6(4,4-dimethyl-3,4-dihydro-6-benzopyranyl) carbonyl 2-formyl naphthalene,
(18) trans 4-(4,4-dimethyl-3,4-dihydro-6-benzopyranyl) carbonyl ethyl α-methyl cinnamate,
(19) trans 4-(4,4-dimethyl-3,4-dihydro-6-benzopyranyl) carbonyl α-methyl cinnamic acid
(20) N-ethyl trans 4-(4,4-dimethyl-3,4-dihydro-6-benzopyranyl) carbonyl α-methyl cinnamide,
(21) trans 4-[(4,4-dimethyl-3,4-dihydro-6-benzothiopyranyl) hydroxymethyl] ethyl α-methyl cinnamate,
(22) trans 4-[(4,4-dimethyl-3,4-dihydro-6-benzothiopyranyl) hydroxymethyl] α-methyl cinnamic acid,
(23) trans 4-(4,4-dimethyl-3,4-dihydro-6-benzothiopyranyl) carbonyl α methyl cinnamic acid,
(24) 6-[(4,4-dimethyl-3,4-dihydro-6-benzopyranyl) hydroxymethyl] 2-napthalene carboxylic acid,
(25) 4-(4,4-dimethyl-3,4-dihydro-6-benzothiopyranyl) hydroxymethyl methyl benzoate,
(26) 4-[(4,4-dimethyl-3,4-dihydro-6-benzothiopyranyl) hydroxymethyl]benzoic acid and
(27) 1-(4,4-dimethyl-3,4,-dihydro-6-benzopyranyl)-1-(6-carboxy-2-naphthyl) methane.

The particularly preferred compounds of those listed above are the following ones:

6-(4,4-dimethy-3,4-dihydro-6-benzopyranyl) carbonyl 2-naphthalene carboxylic acid and 6-(4,4-dimethyl-3,4-dihydro-6-benzothiopyranyl) carbonyl 2-naphthalene carboxylic acid, and their esters and amides, as well as 1-(4,4-dimethyl-3,4-dihydro-6-benzopyranyl)-1-(6-carboxy-2-naphthyl) methane.

The present invention also relates to a process for preparing the compounds of formula I in accordance with the following reaction scheme:

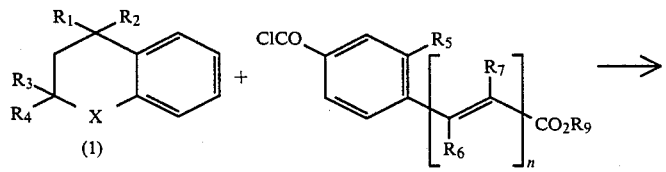

(2) n = 0
(3) n = 1 et $R_5-R_7$ = —CH=CH—

-continued

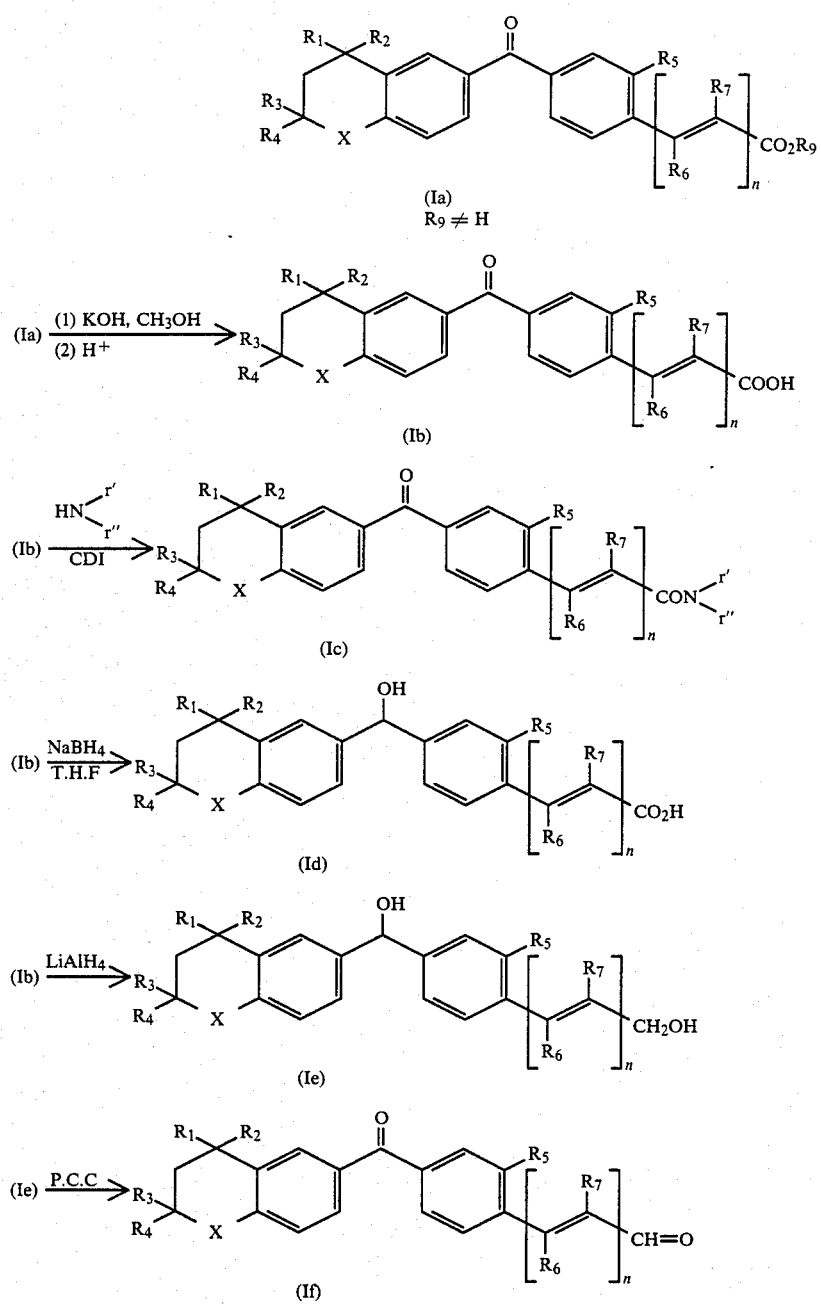

The chloride of 4-alkoxy carbonyl-2-benzoic acid (2) is obtained starting with an alkyl paraformyl benzoate which is oxidized in a corresponding acid using a Jones reactant, then transformed into the acid chloride by the action of thionyl chloride in accordance with known methods for the preparation of acid chlorides.

The chloride of 6-alkoxy carbonyl-2-naphthalene carboxylic acid (3) is obtained by the reaction of thionyl chloride with 6-alkoxy carbonyl-2-napthalene carboxylic acid resulting from the monosaponification reaction of 2,6-alkyl naphthalene dicarboxylate (a commercial product).

The substituted derivatives of chroman and thiochroman, principally the 2,2-dimethyl derivatives (compound of formula (1) with X= —O— or —S—, $R_1=R_2=H$ and $R_3=R_4=CH_3$) and the 4,4dimethyl derivatives (compound of formula (1) with X= —O— or —S—, $R_1=R_2=CH_3$ and $R_3=R_4=H$) are prepared by the method described in J. Med. Chem. (1984) 27, 1516–1531.

The condensation reaction of the chloride of 4-alkoxycarbonyl-2-benzoic acid (2) or of the chloride of 6-alkoxycarbonyl-2-naphthalene carboxylic acid (3) on the chroman or thiochroman, optionally substituted, (1) is carried out under conventional Friedel-Crafts reaction conditions, i.e., in the presence of anhydrous aluminum chloride or anhydrous stannous chloride in 1,2-dichloroethane at a temperature between 0° and 25° C. with stirring.

Starting with the keto-ester (Ia) there is obtained by saponification the corresponding ketoacid (Ib) which can then be transformed into the amide of formula (Ic) by reaction with an amine of the formula

(r' and r" having the meanings given above) in the presence of N, N'-carbonyldiimidazole (CDI).

When $R_9$ represents a monohydroxy or polyhydroxy alkyl radical, it is preferred to prepare the keto-acid (Ib) starting with the methyl ester (Ia) $R_9=CH_3$) and then esterify the resulting keto-acid into the keto-ester of the mono or polyhydric alcohol selected in accordance with known procedures.

Starting with the keto-acid (Ib), the reduction by sodium borohydride in an organic solvent such as THF leads to the secondary alcohol (Id) and the reduction by lithium aluminum hydride of the keto-acid (Ib) leads to the diol (Ie).

On oxidation of the diol (Ie) by pyridinium chlorochromate (PCC) the keto-aldehyde (If) results.

The keto-aldehydes (If) in which n=O constitute starting products for the synthesis of the compounds of formula I wherein n=1 and $R_5$-$R_7 \neq$—CH=CH—.

These compounds are obtained according to the following reaction scheme:

The resulting unsaturated keto-ester (Ig) can then be transformed, as before, into the corresponding acid, then into the amide by reaction with an amine of the formula

or can be reduced by sodium borohydride into a corresponding primary alcohol.

The hydroxyacids of formula (Id) and the corresponding hydroxy esters of formula (I'd), for which n=1, and $R_5=R_6=H$ can be obtained by reacting, an organomagnesium compound prepared from the brominated derivative (2) in position 6 with a -formyl alkyl cinnamate (3) in accordance with the following reaction scheme:

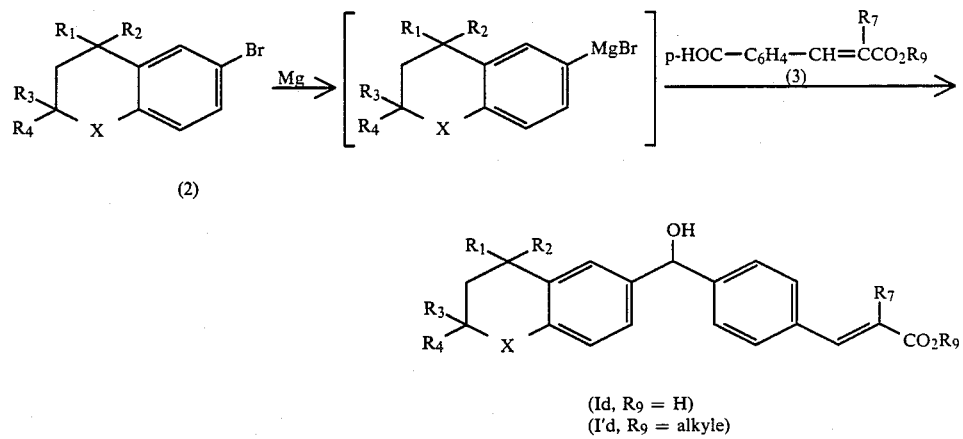

(Id, $R_9$ = H)
(I'd, $R_9$ = alkyle)

The formyl alkyl cinnamates (3) are obtained from commercial terephthaldehyde (4), one of the aldehyde functions being protected in the form of dimethylhydrazone. The aldehyde (5) thus obtained is then condensed on an alkyl phosphonoacetate under the Wittig-Horner reaction conditions and the protected aldehyde function is then freed in an acid medium by exchange with glyoxal to obtain a p-formyl alkyl cinnamate (3).

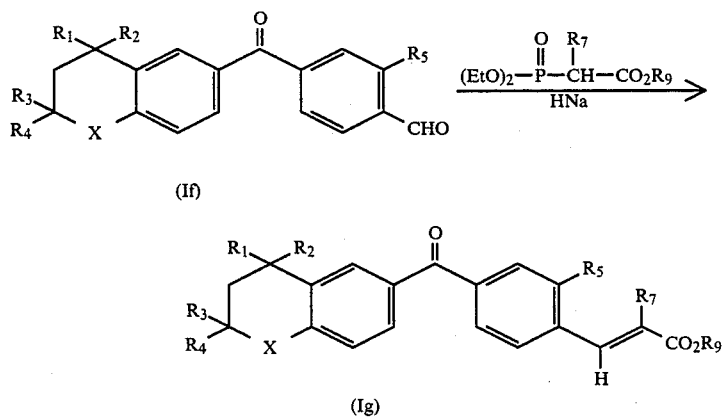

The Wittig-Horner reaction of the keto-aldehyde (If) with phosphono-acetate, substituted or not, is carried out in the presence of sodium hydride in an organic solvent such as THF.

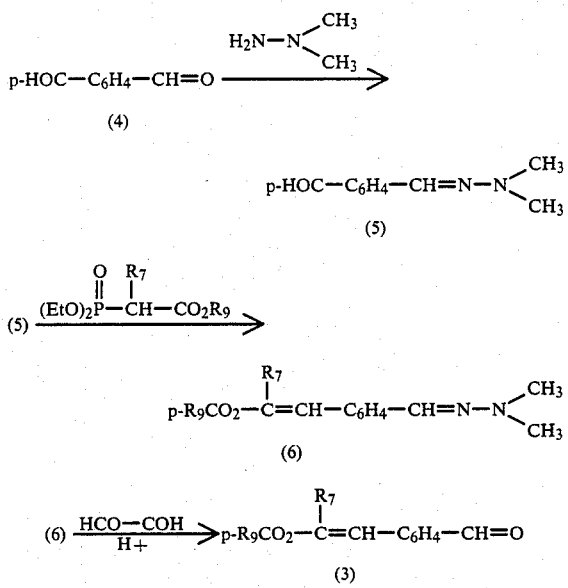

The compounds of formula I, wherein $R'=R''=H$, are obtained by the zinc reduction of ketonic derivatives in acetic acid in the presence of HCl. These reduction reactions of the carbonyl must, however, be compatible with the nature of the R and X radicals. It can be desirable to ensure the optional protection, however the reduction of the carbonyl creates no difficulty when $R=CO_2H$ and $X=-O-$ or $-S-$.

The acyloxy derivatives of the compounds of formula I ($R'=C_1-C_4$ acyloxy and $R''=H$) are obtained by reacting an activated acid form, such as an anhydride or acid chloride with a compound of formula I wherein $R'=OH$ and $R''=H$.

The alkoxy derivatives of the compounds of formula I ($R'=C_1-C_4$ alkoxy and $R''=H$) are also obtained starting with compounds of formula I ($R'=OH$ and $R''=H$) in accordance with known methods.

For the preparation of the acyloxy and alkoxy derivatives it is preferable that the radical R is an ester, acid or amide function.

The present invention further relates to a medicine comprising the compounds of formula I as defined above.

These compounds exhibit excellent activity in the inhibition test of ornithine decarboxylase in nude rats, after induction, by "tape stripping," M. Bouclier, et al, Dermatologica 169, No.4 (1984). This test is recognized as a measure of an antiproliferative activity.

These compounds are particularly appropriate for treating dermatologic ailments linked to a keratinization disorder (differentiation-proliferation) as well as dermatologic diseases, or others, having an inflammatory and/or immunoallergic component, principally:

acne vulgaris, comedons or polymorphs, solar senile acne and medicinal or professional acne, extensive and/or severe forms of psoriasis and other keratinization disorders, and principally ichtysoses and ichtysosis like conditions, Darier malady, palmo-plantar keratodermies, leucophasies and leucophasie-like states, lichen plan, all malignant or benign dermatologic proliferations, severe or extensive.

They are also active in the treatment of tumors, of rheumatoid psoriasis, cutaneous or respiratory atrophies as well as in certain opthalomogic problems relating to corneopathies.

Thus, the present invention also relates to medicinal compositions containing at least one compound of formula (I), such as defined above, or one of its salts or one of its isomers.

The present invention thus relates to a new medicinal composition, intended principally for the treatment of the above-mentioned disorders, comprising in a pharmaceutically acceptable support, an effective amount of at least one compound of formula (I) and/or one of its salts and/or one of its isomers.

The compounds according to the present invention are generally administered at a daily dosage of about 0.01 μg/kg to 1 mg/kg of body weight.

As the vehicle or carrier for these compositions any conventional vehicle can be employed, the active component being found either in the dissolved state, or in the dispersed state in said vehicle.

The administration of the compounds of the present invention can be effected enterally, parenterally, topically or ocularly.

When administered enterally, the medicines can be provided in the form of tablets, gelules, lozenges, syrups, suspensions, solutions, powders, granules or emulsions.

When administered parenterally, the medicinal compositions can be provided in the form of solutions or suspensions for perfusion or injection.

When administered topically, the pharmaceutical compoitions, based on the compounds according to the present invention, can be provided in the form of ointments, tinctures, creams, salves, powders, pads, impregnated tampons, solutions, lotions, gels, sprays or suspensions.

These compositions for topical administration can be provided under anhydrous form or in aqueous form according to clinical indications.

When administered ocularly, the composition is provided principally in the form of an eyewash.

The compositions for topical or ocular administration contain preferably from 0.0001 to about 5 percent by weight of at least one compound of formula (I) such as defined above, and preferably from 0.001 to 1 percent by weight, relative to the total weight of the composition.

The compounds of formula (I), according to the present invention, are also useful in the cosmetic field, in particular in body and hair hygiene compositions and principally for the treatment of skin having acne tendencies, to improve the growth of hair, to combat hair loss, to combat against an oily appearance of the skin or hair, in the prevention or treatment of the harmful effects of the sun or in the treatment of physiologically dry skin.

The present invention thus relates to a cosmetic composition containing, in a cosmetically acceptable vehicle, an effective amount of at least one compound of formula (I) or one of its salts and/or one of its isomers, this composition being provided principally in the form of a lotion, gel, cream, soap or shampoo.

The concentration of the compound of formula (I) in these cosmetic compositions is between 0.0001 and 2 percent by weight and, preferably, between 0.001 and 1 percent by weight based on the total weight of the composition.

The medicinal and cosmetic compositions according to the present invention can contain inert or even pharmacodynamic or cosmetically active additives and, principally: hydrating agents such as thiamorpholinone and its derivatives or urea; antiseborrheic or anti-acne agents such as S-carboxymethylcysteine, S-benzylcysteamine, their salts and their derivatives, tioxolone or benzoyl peroxide; antibiotics such as eythromycin and its esters, neomycin, tetracyclines and 4,5-polymethylene-3-isothiazolones; agents promoting the growth of hair such as "Minoxidil" (2,4-diamino-6-piperdino-3-pyrimidine oxide) and its derivatives, Diazoxide (7-chloro-3-methyl-1,2,4-benzothiadiazine-1,1-dioxide) and Phenytoin (5,5-diphenyl-2,4-imidazolidine dione); steroidal and non-steroidal anti-inflammatory agents; carotenoids and, principally, β-carotene; anti-psoriasic agents such as anthralin and its derivatives and 5,8,11,14-eicosatetraynoic and 5,8,11-eicosatriynoic acids, their esters and their amides.

The compositions according to the present invention can also include flavor improving agents, preservatives, stabilizers, humidity regulating agents, pH regulating agents, osmotic pressure modifying agents, emulsifiers, UV-A and UV-B filters, anti-oxidants such as α-tocopherol, butylhydroxyanisole or butylhydroxytoluene The following non-limiting examples illustrate the preparation of the active compounds of formula (I) according to the present invention as well as compositions containing these compounds.

EXAMPLE A

Preparation of 4-methoxycarbonyl benzoic acid chloride (a) 4 methoxycarbonyl benzoic acid To a solution of 20 g of methyl 4 formyl benzoate in 150 cm$^3$ of acetone, there is slowly added a solution containing 30 g of potassium bichromate in 150 cm$^3$ of water and 27 cm$^3$ of concentrated sulfuric acid. Stirring is maintained for 2 hours at ambient temperature. After evaporation of the acetone under reduced pressure, the reaction mixture is extracted with ethyl acetate. The organic phase is dried on magnesium sulfate and then concentrated, yielding 11 g of crude 4-methoxycarbonyl benzoic acid that is recrystallized in ethyl acetate. The crystals are filtered and dried. The melting point is 222° C. The NMR$^1$ H spectrum corresponds to the expected structure.

(b) ,4-methoxycarbonyl benzoic acid chloride

A suspension of 5 g of the preceding acid in 50 cm$^3$ of thionyl chloride is heated for 3 hours at 40° C. At the end of the reaction, the reaction medium is homogenized and the solution is then concentrated under reduced pressure. The expected acid chloride crystallizes in the form of pink flakes. The yield is quantitative. This solid is employed directly in the condensation reaction.

EXAMPLE B

Preparation of ethyl 4-formyl α-methyl cinnamate (a) mono N, N - dimethylhydrazinoterephthaldehyde To a solution of 75 g of terephthaldehyde in 800 cm$^3$ of anhydrous tetrahydrofuran there is slowly added a solution of 42 cm$^3$ of N,N-dimethylhydrazine in 50 cm$^3$ of tetrahydrofuran in a manner so as to maintain the temperature of the reaction mixture lower than 30° C. At the end of the addition stirring is continued for 2 hours until the total disappearance of the starting terephthaldehyde. After evaporation of the tetrahydrofuran and crystallization of the product in heptane 93 g of mono N,N-dimethylhydrazinoterephthaldehyde are recovered which contains a small amount of di-N,N-dimethylhydrazinoterephthaldehyde. The product is used, as is, for the following preparation.

(b) ethyl 4-(N,N-dimethylhydrazino) formyl α-methyl cinnamate

To a solution of 23 cm$^3$ of 2-triethylphosphono propionate in 400 cm$^3$ of tetrahydrofuran there are added in small portions 4 grams of sodium hydride.

At the end of the addition stirring is maintained for 2 hours. There are then added, in the absence of light, 12 g of mono(N,N-dimethyl hydrazino) terephthaldehyde prepared in steps (a) above, in solution in 100 cm$^3$ of tetrahydrofuran in a manner to maintain the temperature lower than 30° C.

At the end of the addition, stirring is maintained for about 1 hour until the total disappearance of the starting aldehyde. The reaction mixture is poured over a solution of ammonium chloride and extracted with ethylacetate. The organic phases are washed, dried on magnesium sulfate and concentrated under reduced pressure. 15 g of an oil are recovered whose NMR$^1$H spectrum 80 MHz corresponds to the expected structure and which is used, in this crude form, for the following preparation.

(c) ethyl 4-formyl α-methyl cinnamate

To a solution of 12 g of ethyl 4-(N,N-dimethylhydrazino) formyl α-methyl cinnamate prepared in step (b) above, in 150 cm$^3$ of toluene, 28 cm$^3$ of aqueous glyoxal (6.2M) and about 1 cm$^3$ of concentrated HCl are added. The solution is heated at 70° C. for about 2 hours until the disappearance of the starting product. The organic phase is decanted, washed with water, dried on magnesium sulfate and concentrated under reduced pressure.

After purification by chromatography on silica gel (eluant:8/2, hexane/ethylacetate) 6 g of ethyl 4-formyl α-methyl cinnamate are recovered whose NMR$^1$H spectrum 80 MHz corresponds to the expected structure. Melting point: 42°–43° C.

EXAMPLE I

Preparation of 4-(4,4 dimethyl-3,4-dihydro-6- benzopyranyl)) carbonyl methyl benzoate. Compound of formula II wherein n=0, X=—O—, R' and R"=oxo and R$_8$=—OCH$_3$.

To a solution, stirred at a temperature of 5° C., of 4 g (0.0246 mole) of 4,4-dimethyl-3,4-dihydro-benzopyran and 5.9 g (0.0296 mole) of 4-methoxycarbonyl benzoic acid chloride in 120 cm$^3$ of anhydrous 1,2-dichloroethane, these are added, in small portions, 7.3 g (0.0543 mole) of aluminum chloride. Stirring is continued for ½ hour after the end of the addition. After standing overnight at ambient temperature, the mixture is poured over ice. The organic phase is decanted and the aqueous phase is extracted with dichloromethane. The combined organic phases are washed with a solution of sodium bicarbonate, dried on magnesium sulfate and concentrated under reduced pressure. The resulting solid is powdered in hexane. The crystals are filtered and dried yielding 5 g of white crystals having a melting point of 102° C.

EXAMPLE II

Preparation of 4-(4,4-dimethyl-3,4-dihydro-6-benzopyranyl) carbonyl benzoic acid.

Compound of formula II wherein n=0, X=—0—, R' and R"=oxo and R$_8$=OH.

A mixture of 4.3 g of the ester obtained in Example I and 1.3 g of 85% potash in 80 cm³ of ethanol is heated at reflux for 2 hours. The ethanol is then removed by evaporation under a vacuum. The residue is taken up in 100 cm³ of water and acidified by the addition of concentrated HCl. The expected acid precipitates. It is filtered, dried and then recrystallized in a diisopropyl ether/DMF mixture. 2.5 g of 4-(4,4-dimethyl-3,4-dihydro-6-benzopyranyl) carbonyl benzoic acid having a melting point of 199° C. are isolated. The NMR1H spectrum conforms to the expected structure.

Elemental Analysis: $C_{19}H_{18}O_4$ Calculated: C: 73.53 H: 5.85 O: 20.62 Found: 73.52; 5.85; 20.68;

EXAMPLE III

Preparation of N-ethyl 4-(4,4-dimethyl-3,4 dihydro-6-benzopyranyl) carbonyl benzamide. Compound of formula II wherein n=0, X=—O—, R' and R''=oxo and $R_8$=NHC$_2$H$_5$.

To a suspension of 1g of the acid obtained in Example II in 100 cm³ of anhydrous dichloromethane, there is added 0.750 g (1.4 equivalents) of carbonyl diimidazole. Stirring of the solution is maintained for 1 hour at which point 2.5 cm³ of anhydrous ethylamine are added. The reaction mixture is left overnight. The dichloroethane phase is washed with a solution of ammonium chloride, dried and then concentrated under reduced pressure.

The expected product is purified by silica gel chromatography (eluant, 8/2 hexane/ethylacetate).

A white powder, having a melting point of 140° C. is obtained. The NMR1H spectrum corresponds to N-ethyl 4-(4,4-dimethyl-3,4-dihydro-6-benzopyranyl) carbonyl benzamide.

EXAMPLE IV

Preparation of 4-(4,4-dimethyl-3,4-dihydro-6-benzothiopyranyl) carbonyl methyl benzoate. Compound of formula II wherein n=0, X=—S—, R' and R''=oxo and $R_8$=—OCH$_3$ To a solution, stirred at a temperature of 5° C., of 2.45 g (0.0123 mole) of 4-methoxy carbonyl benzoic acid chloride and 2 g (0.0112 mole) of 4,4-dimethyl-3,4-dihydrobenzothiopyran in 25 cm³ of anhydrous 1,2-dichloroethane, there are slowly added 1.8 cm³ of stannous chloride. The reaction mixture is left to stand for 24 hours at ambient temperature. 30 cm³ of 2N HCl solution are then added.

The organic phase is decanted and the aqueous phase is extracted with dichloromethane. The organic phases are combined, then washed with a sodium bicarbonate solution and dried on magnesium sulfate.

On concentration of the organic phases under reduced pressure and treatment of the crude reaction mixture with hot hexane 1.1 g of white crystals having a melting point of 85° C. are obtained.

The NMR1H spectrum corresponds to 4-(4,4-dimethy-3,4-dihydro-6-benzothiopyranyl) carbonyl methyl benzoate.

EXAMPLE V

Preparation of 4-(4,4-dimethyl-3,4-dihydro-6-benzothiopyranyl) carbonyl benzoic acid. Compound of formula II wherein n=O, X=—S—, R' and R''=oxo and $R_8$=OH.

A mixture of 1g of the ester obtained in Example IV and 500 mg of 85% potash in 50 cm³ of ethanol is heated at reflux for 2 hours. The ethanol is then removed by evaporation under a vacuum. The residue is taken up in 75 cm³ of water and acidified by the addition of concentrated HCl. The expected acid precipitates. It is filtered, dried and then recrystallized in a diisopropylethermethylethylketone mixture. 500 mg of 4-(4,4-dimethyl-3,4-dihydro-6-benzothiopyranyl) carbonyl benzoic acid having a melting point of 211° C. are recovered.

The NMR1H spectrum 250 MHz corresponds to the expected structure.

Elemental anaylsis: $C_{19}H_{18}O_3S$ Calculated: C: 69.91; H: 5.56; O: 14.71; S: 9.82; Found 69.68; 5.50; 14.38; 9.77.

EXAMPLE VI

Preparation of 6-(4,4-dimethyl-3,4-dihydro-6-benzothiopyranyl) carbonyl 2 methyl naphathalene carboxylate. Compound of formula III wherein X=—S—, $R_1$=$R_2$=CH$_3$, $R_3$=$R_4$=H, R' and R''=oxo and $R_8$=OCH$_3$ To a solution of 7.2 g (0.04 mole) of 4,4-dimethy-3,4-dihydrobenzothiopyran (4,4-dimethylthiocleroman) and 10 g (0.04 mole) of 6-methoxycarbonyl 2 naphthalene carboxylic acid chloride in 800 cm³ of anhydrous dichloroethane, there are added, in small portions, 8.05 g (0.06 mole) of anhydrous aluminum chloride. The mixture is left overnight at ambient temperature and then poured into 1000 cm³ of ice water. The organic phase is decanted. The aqueous phase is extracted with 300 cm³ of dichloromethane. The organic phases are combined, washed with sodium bicarbonate, dried on magnesium sulfate and then concentrated under reduced pressure. The expected product is purified by silica gel chromatography (eluant: dichloromethane/hexane). After recrystallization in acetonitrile 5.2 g of 6-(4,4-dimethyl-3,4-dihydro-6-benzothiopyranyl) carbonyl 2-methyl naphthalene carboxylate are obtained. The resulting product is a white powder whose melting point is 136°-138° C.

Elemental analysis: $C_{24}H_{22}O_3S$ Calculated: C 73.81; H 5.68; O 12.29; S 8.21; Found 73.60; 5.66; 12.02; 8.10; 8.33.

EXAMPLE VII

Preparation of 6-(4,4-dimethyl3,4-dihydro-6-benzothiopyranyl) carbonyl 2-naphthalene carboxylic acid. Compound of formula III wherein X=—S—, $R_1$=$R_2$=CH$_3$, $R_3$=$R_4$=H, R' and R''=oxo and $R_8$=OH A suspension of 4.5 g of 6-(4,4 dimethyl-3,4-dihydro-6-benzothiopyranyl) carbonyl 2-methyl naphthalene carboxylate obtained in Example VI is stirred for one-quarter hour in a mixture of 100 cm³ of ethanol and 100 cm³ of 6N aqueous potash at a temperature between 50° and 60° C. After having added 100 cm³ of water, the ethanol is removed by evaporation under a vacuum. The resulting aqueous phase is cooled to between 0° and 5° C., then acidified to pH=1 by the addition of 6N HCl. The resulting precipitate is filtered, washed with water and dried at 80° C. on potash.

After recrystallization in methylethylketone 1.8 g of 6-(4,4-dimethyl-3,4-dihydro-6-benzothiopyranyl) carbonyl 2-naphthalene carboxylic acid are obtained. The product is a white powder whose melting point is from 258°-259° C.

The NMR1H spectrum 250 MHz conforms to the expected structure.

Elemental anaylsis: $C_{23}H_{20}O_3S$ Calculated: C; 73.37; H: 5.35; O: 12.75; S: 8.50; Found 73.47; 5.41; 12.94; 8.36.

EXAMPLE VIII

Preparation of N-ethyl-6-(4,4-dimethyl-3,4-dihydro-6-benzothiopyranyl) carbonyl 2-naphthalene carboxamide Compound of formula III wherein X=—S—, $R_1=R_2=CH_3, R_3=R_4=H$, R' and R"=oxo and $R_8=NH-C_2H_5$ A suspension of 500mg (1.32 mmoles) of 6-(4,4-dimethyl -3,4-dihydro-6-benzothiopyranyl) carbonyl-2-naphthalene carboxylic acid obtained in Example VII and 240 mg (1.5 mmoles) of N,N'-carbonyl diimidazole in 50 cm³ of anhydrous dichloromethane is stirred for 3 hours at ambient temperature. There is then added 0.50 cm³ (excess) of anhydrous ethylamine to the resulting solution. After stirring for 3 hours, the reaction mixture is poured into 100 cm³ of water and extracted with dichloromethane.

The organic phase is washed with 50 cm³ of 1N HCl and 50 cm³ of water, then dried on magnesium sulfate and evaporated to dryness. The crude amide is purified by silica gel chromatography (eluant: dichloromethane/ethylacetate), yielding 400 mg of white powder of N-ethyl 6-(4,4-dimethyl-3,4-dihydro -6-benzothiopyranyl) carbonyl-2-naphthalene carboxamide whose melting point is from 208°–209° C.

The NMR'H spectrum 250 MHz conforms to the expected structure.

Elemental analysis: $C_{25}H_{25}NO_2S$ Calculated: C: 74.71; H: 6.24; N: 3.41; O: 7.93 S: 7.93; Found 74.31. 6.25; 3.39; 7.80; 7.88.

EXAMPLE IX

Preparation of 6-(2,2-dimethyl-3,4-dihydro 6-benzopyranyl) carbonyl 2-methyl naphothalene carboxylate. Compound of formula III wherein X=—O—, $R_1=R_2=H$, $R_3=R_4=3$, R' and R"=oxo and $R_8=OCH_3$.

To a suspension of 1.62 g (10 moles) of 2,2-dimethyl-3,4-dihydro-benzopyran and 2.5 g (10 moles) of 6-methoxycarbonyl-2-naphthalene carboxylic acid chloride in 60 cm³ of anhydrous 1,2-dichloroethane, there are added, by portions, over a 45-minute period, 2 g (15 moles) of anhydrous aluminum chloride. The mixture is stirred for 5 hours at ambient temperature and then poured into 150 cm³ of acidulated ice water. The organic phase is decanted. The aqueus phase is extracted once more with 100 cm³ of 1,2-dichloroethane. The dichloroethane phases are combined, washed with sodium bicarbonate, dried on sodium sulfate and then concentrated. The resulting crude solid is purified by silica gel to chromatography in a 70/30 mixture of dichloromethane/toluene and then recrystallized in isoproponal. 1.4 g of white crystals of 6-(2,2-dimethyl-3,4-dihydro-6-benzopyranyl) carbonyl 2-methyl naphthalene carboxylate whose melting point is 167° C. are obtained.

The NMR'H spectrum 60 MH3 conforms to the expected structure.

Elemental analysis: $C_{24}H_{b\ 22}O_4$ Calculated: C; 76.98H; 5.92; O; 17.09; Found: 76.87; 5.90; 16.94.

EXAMPLE X

Preparation of 6-(4,4-dimethyl-3,4-dihydro-6-benzopyranyl)-carbonyl-2-methyl naphthalene carboxylate. Compound of formula III wherein X=—O—, $R_1=R_2—CH_3$, $R_3=R_4=H$, R' and R" =oxo and $R_8=OCH_3$. =oxo and $R_8=OCH_3$.

To a suspension of 1.4 g (8.6 mmoles) of 4,4-dimethyl-3,4-dihydrobenzopyran and 2.15 g (8.6 mmoles) of 6-methoxycarbonyl-2-naphthalene carboxylic acid chloride in 40 cm³ of 1,2-dichlorethane, there are added, by portions over a 40 minute period, 1.6 g (12 mmoles) of anhydrous aluminum chloride. The mixture is stirred for 4 hours at ambient temperature and then poured into 100 cm³ of acidulated ice water. The organic phase is decanted. The aqueous phase is again extracted with 100 cm³ of 1,2-dichloroethane. The dichloroethane phases are combined, washed with sodium bicarbonate, dried on sodium sulfate and then concentrated. The resulting solid is purified by silica 60 chromatography in a 70/30 mixture of dichloromethane/toluene. 1.25 g of white crystals of 6-(4,4-dimethyl-3,4-dihydro-6-benzopyranyl) carbonyl 2-methyl naphthalene carboxylate whose melting point is 129° C. are obtained.

The NMR¹H spectrum 60 MHz conforms to the expected structure.

Elemental analysis: $C_{24}H_{22}O_4$ Calculated: C: 76.98 H: 5.92; O: 17.0; Found C: 76.84; H: 5.9; O: 17.15.

EXAMPLE XI

Preparation of 6-(2,2-dimethyl-3,4-dihydro-6-benzopyranyl) carbonyl 2-naphthalene carboxylic acid. Compound of formula III wherein X=—O—, $R_1=R_2=H$, $R_3=R_4=CH_3$, R' and R"=oxo and $R_8=OH$ A suspension of 0.9 g (2.4 mmoles ) of 6-(2,2-dimethyl-3,4-dihydro-6-benzopyranyl) carbonyl-2-methyl naphthalene carboxylate obtained in Example IX is stirred for 2 hours in a mixture of 15 cm³ of alcohol and 15 cm³ of 6N aqueous potash heated at reflux. After having added 100 cm³ of water, the alcohol is removed by evaporation under a vacuum. The aqueous phase thus obtained is diluted to 250 cm³, cooled to between 0° and 5° C. and then acidified by the addition of 15 cm³ of 12N HCl. The resulting precipitate is filtered, washed with water and dried at 80° C. on potash.

After recrystallization in 60 cm³ of isopropanol and then in 100 cm³ of methanol 0.66 g of white crystals of 6-(2,2-dimethyl-3,4-dihydro-6-benzopyranyl) carbonyl 2-naphthalene carboxylic acid whose melting point is 269° C. is obtained.

The NMR¹H spectrum 250 MHz conforms to the expected structure.

Elemental analysis: $C_{23}H_{20}O_4$ Calculated: C: 1 76.65; H: 5.59 O: 17.76; Found: 76.65; 5.63; 17.70.

EXAMPLE XII

Preparation of 6-(4,4-dimethyl-3,4-dihydro-6-benzopyranyl) carbonyl-2-naphthalene carboxylic acid. Compound of formula III wherein X=—O—, $R_1=R_2=CH_3$, $R_3=R_4=H$, R' and R"=oxo and $R_8=OH$ A suspension of 0.9 g (2.4 mmoles) of 6-(4,4-dimethyl-3,4-dihydro-6-benzopyranyl) carbonyl-2-methyl naphthalene 2-methyl naphthalene carboxylate obtained in Example X is stirred for 2 hours in a mixture of 15 cm³ of alcohol and 15 cm³ of 6N aqueous potash heated at reflux. After having added 100 cm³ of water, the alcohol is removed by evaporation under a vacuum. The aqueous phase thus obtained is diluted to 200 cm³, cooled to between 0° and 5° C. and then acidified by the addition of 15 cm³ of 12N HCl. The resulting precipitate is filtered, washed with water and dried at 80° C. on potash.

After recrystallization in 40 cm³ of isopropanol 0.68 g of white crystals of 6-(4,4-dimethyl-3,4-dihydro-6-benzopyranyl ) carbonyl 2-naphthalene carboxylic acid whose melting point is 253° C. is obtained.

The NMR¹H spectrum 250 MHz conforms to the expected structure.

Elemental analysis: $C_{23}H_{20}O_4$ Calculated: C: 76.65; H: 5.59; O: 17.76 Found: 76.70; 5.66; 17.81.

EXAMPLE XIII

Preparation of trans 4-[(4,4-dimethyl-3,4-dihydro-6-benzothiopyranyl hydroxymethyl]ethyl-4- ''-methyl cinnamate Compound of formula II wherein X=—S—, n=1, R'=OH, R''=H and $R_8$—$OC_2H_5$ A solution of 2.7 g (0.0105 mole) of 6-bromo-4,4-dimethyl-3,4-dihydrobenzothiopyran in 75 cm³ of anhydrous tetrahydrofuran is added to 700 mg of magnesium. Reflux is maintained until the disappearance of the magnesium.

The reaction mixture is then cooled to 0° C. and there is slowly added a solution of 11 g of 4-formyl ethyl α-methyl cinnamate obtained in Example B in 20 cm³ of tetrahydrofuran. At the end of the addition the mixture is maintained under stirring at 0° C. for about 30 minutes and then at ambient temperature for 2 hours. The reaction mixture is poured into 200 cm³ of a saturated solution of ammonium chloride and extracted with ether. The organic phase is washed, dried on magnesium sulfate and then concentrated under reduced pressure.

The expected product is purified by silica gel chromatography (eluant: 9/1 heptane - ethyl acetate).

1.9 g of an oil whose NMR¹H spectrum 80 MHz corresponds to the structure of trans 4-[(4,4-dimethyl-3,4-dihydro-6-benzothiopyranyl hydroxymethyl]ethyl α-methyl cinnamate are recovered.

EXAMPLE XIV

Preparation of trans 4-[(4,4-dimethyl -3,4-dihydro-6-benzothiopyranyl) hydroxymethyl]α-methyl cinnamic acid. Compound of formula II wherein X=—S—, n=1, R'=OH, R''=H, $R_8$=OH.

A solution of 1.8 g of trans 4-[4,4-dimethyl (3,4-dihydro-6-benzothiopyranyl) hydroxymethyl]ethyl α-methyl cinnamate obtained in EXAMPLE XIII is heated at 40° C., in a mixture of 200 cm³ of ethyl alcohol and 100 cm³ of 6N aqueous potash until the disappearance of the starting product.

The ethanol is evaporated under reduced pressure and the residue is taken up in 300 cm³ of water. The mixture is cooled to 0° C. and acidified with a 3N solution of HCl.

The expected product is extracted with ethyl ether and the organic phase is washed, dried on magnesium sulfate and then concentrated under reduced pressure.

On recrystallization in hexane 1.1 g of trans 4-[(4,4-dimethyl-3,4-dihydro-6benzothiopyranyl) hydroxymethyl]α-methyl cinnamic acid having a melting point of 135° C. are recovered.

EXAMPLE XV

Preparation of 6-[(4,4-dimethyl-3,4-dihydro-6-benzopyranyl) hydroxymethyl]2-naphthalene carboxylic acid. Compound of formula III wherein X=—O—, $R_1$=$R_2$=$CH_3$, R'=OH, R''=OH, R'''=H, $R_3$=$R_4$32 H and $R_8$50 OH.

To a solution of 0.72 g (2 mmoles) of 6-(4,4-dimethyl-3,4-dihydro-6-benzopyranyl) carbonyl 2-naphthalene carboxylic acid in 25 cm³ of anhydrous tetrahydrofuran, stirred at ambient temperature, there is added 0.3 g (8 mmoles) of sodium borohydride.

After overnight stirring, the reaction mixture is cooled to between 0 and 5° C., acidified by the slow addition of 0.1 N HCl and extracted with ethyl ether. The organic phase is washed with water, dried on sodium sulfate and evaporated to dryness.

After recrystallization in a hexane/ethyl acetate mixture, 0.65 g of white crystals of 6-[(4,4-dimethyl-3,4-dihydro-6-benzopyranyl) hydroxymethyl]2-naphthalene carboxylic acid having a melting point of 173°–174° C. is obtained.

The IR and NMR¹H spectra 80 MHz conform to the expected structure.

EXAMPLE XVI

Preparation of 4-(4,4-dimethyl-3,4-dihydro-6-benzothiopyranyl) hydroxymethyl methyl benzoate. Compound of formula II wherein X=—S—, n=0, R'=OH, R''=H and $R_8$=$OCH_3$.

To a solution of 5 g (0.0195 mole) of 6-bromo-4,4-dimethyl-3,4-dihydro benzothiopyran in 50 cm³ of anhydrous THF, there is added 0.55 g of magnesium. The reaction is primed by heating. The reaction medium is maintained at the reflux of THF for about 1 hour until the total disappearance of magnesium.

The reaction mixture is cooled to 0° C. and in the absence of air, the organomagnesium compound is decanted in a dropping funnel. The product is slowly added to a solution of 1.8 g of 4 formyl methyl benzoate in about 150 cm³ of anhydrous THF at 0° C. During the addition, the temperature must not exceed 5° C. At the end of the addition, the reaction mixture is maintained under stirring of 2 hours and then left overnight.

The reaction mixture is poured into 100 cm³ of a saturated ammonium chloride solution and then extracted with 3×100 cm³ of ethyl ether.

The organic phase is washed with a diluted solution of ammonium chloride, then with water, dried on magnesium sulfate and concentrated under reduced pressure.

The expected product is purified by silica gel chromatography (eluant: 8/2, heptane/ethylacetate). acetate).

1.3 g of a pure yellow oil whose NMR¹H spectrum 80 MHz conforms to the expected structure.

EXAMPLE XVII

Preparation of 4-(4,4-dimethyl-3,4-dihydro-6-benzothiopyranyl) hydroxymethyl benzoic acid. Compound of formula II wherein X=—S—, n=0, R'=OH, R''=H and $R_8$=OH To a solution of 1 g of 4-(4,4 dimethyl-3,4-dihydro-6-benzothiopyranyl ) hydroxymethyl methylbenzoate in 100 cm³ of ethyl alcohol, there are added 30 cm³ of a 6N aqueous potash solution. The reaction mixture is maintained under stirring, at about 40° C., for 1 hour, until the total disappearance of the starting product.

The alcohol is evaporated under reduced pressure, the aqueous phase is diluted with 100 cm³ of water, cooled to 0° C. and acidified with concentrated HCl. The resulting precipitate is filtered, washed with water and dried. The expected acid is purified by recrystallization in a toluene/hexane mixture. 600 mg of a white powder melting at 139° C. are recovered.

The NMR¹H spectrum 80 MHz conforms to the structure of 4-(4,4-dimethyl-3,4-dihydro-6benzothiopyranyl) hydroxymethyl benzoic acid.

Elemental analysis: $C_{19}H_{20}O_3S$ Calculated: C: 69.48; H: 6.14 O: 14.62 S: 9.76 Found: 69.05; 6.22; 14.17; 9.04

EXAMPLE XVIII

Preparation of 4-(4,4-dimethyl-3,4-dihydro-1,1-dioxide-6-benzothiopyranyl) carbonyl benzoic acid. Compound of formula II wherein

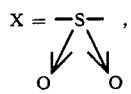

$n=0$, R' and R''=oxo and $R_8$=OH.

To a solution of 300mg of 4-(4,4-dimethyl-3,4-dihydro-6-benzothiopyranyl) carbonyl benzoic acid in 50 cm³ of formic acid there is added 0.25 cm³ of 30% $H_2O_2$. The reaction mixture is maintained under stirring for 4 hours and then the formic acid is partically evaporated. The residue is taken up in water and the expected product is extracted with 3×50 cm³ of ethyl acetate. The organic phase is thoroughly washed, then dried on magnesium sulfate and concentrated under reduced pressure.

The residue is crystallized in a hexane/toluene mixture. 250 mg of 4-(4, 4 - dimethyl-3,4-dihydro-1,1-dioxide-6-benzothiopyranyl) carbonyl benzoic acid whose melting point is 175° C. are recovered.

The NMR¹H spectrum 80 MHz is in agreement with the expected structure.

EXAMPLE XIX

Preparation of N-ethyl 6-(4,4-dimethyl-3,4-dihydro-6-benzopyranyl) carbonyl-2-naphthalene carboxamide. Compound of formula III wherein X=—O—, $R_1=R_2=CH_3$, $R_3=R_4=H$, R' andR''=oxo and $R_8$=NHet.

A suspension of 1.98 g (5.5 mmoles) of 6-(4,4-dimethyl-3,4-dihydro-6-benzopyranyl) carbonyl 2-naphthalene carboxylic acid and 1.07 g (6.6 mmoles) of N,N'-carbonyl diimidazole in 50 cm³ of anhydrous dichloromethane is stirred for 1 hour at ambient temperature. There is then added 0.5 cm³ (7.15 mmoles) of anhydrous ethylamine to the resulting solution and the solution is stirred for 3 hours at ambient temperature. The reaction mixture is diluted with 30 cm³ of dichloromethane, then washed successively with 25 cm³ of N HCl and then 3 times with 25 cm³ of water. The dichloromethane phase is dried on sodium sulfate and evaporated to dryness under reduced pressure. The crude amide is purified by silica 60 gel chromatography using an eluant mixture of 2/8/90 acetic acid/dioxane/toluene followed by recrystallization in a mixture of isopropylether/acetone. After drying, 1.1 g of N-ethyl 6-(4,4-dimethyl-3,4-dihydro-6-benzopyranyl) carbonyl-2-naphthalene carboxamide in the form of a white solid having a melting point of 174° C. are obtained.

The NMR¹H spectrum 250 MHz conforms to the expected structure.

Elemental analysis: $C_{25}H_{25}NO_3$ Calculated: C: 77.49 H: 6.50 N: 3.61 O: 12.39 Found: 77.31; 6.55; 3.70; 12.67.

EXAMPLE XX

Preparation of N-ethyl 6-(4,4-dimethyl-3,4-dihydro-6-benzopyranyl) hydroxymethyl 2-naphthalene carboxamide. Compound of formula III wherein X=—O—, $R_1=R_2=CH_3$, $R_3=R_4=H$, R'=OH, OH, R''=H and $R_8$=NHEt.

To a solution of 116 mg (0.3 mmole) of N ethyl 6-(4,4 dimethyl -3,4 - dihydro -6benzopyranyl) carbonyl-2-naphthalene carboxamide in 10 cm³ of anhydrous tetrahydrofuran, there are added 45 mg (1.2 mmoles) of sodium borohydride. The reaction mixture is heated at reflux with stirring until complete transformation (12 hours ). The reaction mixture is then cooled to between 0° and 5° C., acidified by the slow addition of 0.1N HCl and then extracted with ethyl ether. The organic phase is washed with water, dried on sodium sulfate and evaporated to dryness. The waxy solid obtained is purified by silica 60 chromatography (20 g) in an eluant mixture of toluene/dichloromethane/ethylacetate, 30/40/30, followed by recrystallization in hexane containing a trace of acetone. After drying, 90 mg of white crystals of N-ethyl 6-(4,4-dimethyl-3,4-dihydro-6-benzopyranyl) hydroxymethyl 2-naphthalene carboxamide whose melting point is 92°–95° C. are obtained.

The NMR¹H spectrum 250 MHz conforms to the expected structure.

Elemental analysis: $C_{25}H_{27}NO_3$ Calculated: C: 77.09 H: 6.99 N: 3.60 O: 12.32 Found: 77.11; 6.99; 3.72; 12.48.

EXAMPLE XXI

Preparation of 1-(4,4-dimethyl-3,4-dihydro-6-benzopyranyl)-1-(6-carboxy-2-naphthyl) methane. Compound of formula III wherein X=—O—, $R_1=R_2=CH_3$ $R_3=R_4=H$, R'=R''=H and $R_8$=OH.

To a suspension of 1 g (15 mmoles) of powdered zinc in 10 cm³ of glacial acetic acid, there are added 360 mg (1 mmole ) of 6-(4,4-dimethyl-3,4-dihydro-6-benzopyranyl) carbonyl-2-naphthalene carboxylic aid. The reaction mixture is heated for 1 hour at reflux. There are then slowly added 1.5 cm³ of 12 N HCl and the mixture is maintained at reflux for 30 minutes. After cooling to ambient temperature and adding 20 cm³ of 6N HCl, the reaction mixture is extracted with dichloromethane (2×25 cm³). The organic phase is washed with water, dried on sodium sulfate and concentrated under reduced pressure. The resulting crude yellow solid is purified by silica 60 gel chromatography in an eluant mixture of dichloromethane/tetrahydrofuran, 95/5, followed by recrystallization on a hexane/acetone mixture. After drying, 210 mg of white needles of 1-(4,4-dimethyl-3,4-dihydro-6-benzopyranyl)-1-(6-carboxy-2-naphthyl) methane have a melting point of 202° C. are obtained.

The NMR¹H spectrum 80 MHz conforms to the expected structure.

Elemental analysis: $C_{23}H_{22}O_3$ Calculated: C:79.74 H:6.40 O:13.86 Found: 79.67; 6.28; 13.98.

EXAMPLE XXII

Preparation of 6-(4,4-dimethyl-3,4-dihydro-6-benzopyranyl) hydroxymethyl-2-naphthalene carbinol. Compound of formula I wherein X=—O—, n=1, $R_1=R_2=CH_3$, $R_3=R_4=$
$R_6=H$, R'=OH, R''=H, $R_5$ -$R_7$=—CH=CH and R=—$CH_2OH$ To a suspension of 125 mg (3 mmoles) of lithium aluminum hydride in 20 cm³ of anhydrous tetrahydrofuran, cooled to −20° C., these are added by portions, over a 5 minute period, 360 mg (1 mmole) of 6-(4,4-dimethyl-3,4-dihydro-6-benzopyranyl) carbonyl-2-naphthalene carboxylic acid. After two hours of stirring while leaving it to return to ambient temperature, the reaction mixture is cooled to 0° C., acidified by the slow addition of 0.1 N HCl, and extracted with ethyl ether. The organic phase is washed with water, dried on sodium sulfate and evaporated to dryness. The crude product is purified by silica 60 gel chromatogrphy in an eluant mixture of acetic acid/dioxane/toluene, 2/8/90. After evaporation and prolonged drying, 0.26 g of 6-(4,4-dimethyl-3,4-dihydro-6-benzopyranyl) hydroxymethyl 2-naphthalene carbinol in the form of a colorless thick oil is obtained.

The NMR$^1$H spectrum 80 MHz conforms to the expected structure.

Elemental analysis: $C_{23}H_{24}O_3$ Calculated: C: 79.28 H:6.94 O: 13.78 Found 79.14; 6.90; 14.02.

During the course of the chromatography 50 mg of 6-(4,4-dimethyl-3,4-dihydro-6-benzopyranyl) carbonyl-2-formyl naphthalene whose preparation is described in EXAMPLE XXIII are also separated.

EXAMPLE XXIII

Preparation of 6-(4.4-dimethyl-3,4dihydro-6-benzopyranyl) carbonyl-2formyl naphthalene. Compound of formula III wherein $X=-O-$, $R_1=R_2=CH$, $R_3=R_4=R_8=H$, and R' and R''=oxo.

To a solution of 120 mg (0.34 mmole) of 6(4,4-dimethyl-3,4-dihydro-6-benzopyranyl) hydroxymethyl-2-naphthalene carbinol, described in EXAMPLE XXII, there are added 200 mg (1.03 mmoles) of pyridinium chlorochromate, the reaction mixture is stirred for 40 minutes at ambient temperature. The reaction mixture is then evaporated to dryness and chromatographed on silica 60 in an eluant mixture of acetic acid/dioxane/toluene, 2/8/90. After evaporation, the recovered solid is recrystallized in hexane containing a trace of acetone. After drying, 70 mg of white crystals of 6-(4,4-dimethyl-3,4-dihydro-6-benzopyranyl) carbonyl 2-formyl naphthalene having a melting point of 151° C. are obtained.

The NMR$^1$H spectrum 250 MHz conformed to the expected structure.

EXAMPLES OF COMPOSITIONS

Oral Compositions

EXAMPLE 1–0.2 g tablet

| | |
|---|---|
| 4-(4,4-dimethyl-3,4-dihydro-6-benzopyranyl) carbonyl benzoic acid - Example II | 0.005 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.0005 g |

In this Example, the active compound can be replaced by the same amount of the compound of Example VII.

EXAMPLE 2

| | |
|---|---|
| Drinkable suspension in 5 ml ampoules N—ethyl-4-(4,4-dimethyl-3,4,-dihydro-6-benzopyranyl) carbonyl benzamide - Example III | 0.001 g |
| Glycerine | 0.500 g |
| Sorbitol, 70% | 0.500 g |
| Sodium saccharinate | 0.010 g |
| Methyl parahydroxybenzoate | 0.040 g |
| Flavoring agent, sufficient amount | |
| Purified water, sufficient amount for 5.000 ml | |

In this Example, the active compound can be replaced by the same amount of the compound of Example VI.

B. Topical Compositions

EXAMPLE 3—

Ointment

| | |
|---|---|
| 4-(4,4-dimethyl-3,4,-dihydro-6-benzothiopyranyl) carbonyl benzoic acid - Example V | 0.020 g |
| Isopropylmyristate | 81.700 g |
| Fluid petrolatum oil | 9.100 g |
| Silica, sold under the trade name "Aerosil 200" by Degussa | 9.180 g |

In this Example the active compound can be replaced by 0.005 g of the compound of Example II.

EXAMPLE 4—

Anti-seborrhea cream

| | |
|---|---|
| Polyoxyethylenated stearate (40 moles of ethylene oxide) sold under the trade name "Myrij 52" by Atlas | 4.00 g |
| Mixture of lauryl esters of sorbitol and sorbitan, polyoxyethylenated with 20 moles of ethylene oxide, sold under the trade name "Tween 20" by Atlas | 1.8 g |
| Mixture of mono- and distearate of glycerol, sold under the trade name "GELEOL" by Gattefosse | 4.2 g |
| Propylene glycol | 10.0 g |
| Buhyhydroxyanisole | 0.01 g |
| Buyhydroxytoluene | 0.02 g |
| Cetyl-stearyl alcohol | 6.2 g |
| Preservative, sufficient amount | 18 g |
| Perhydrosqualene | |
| Mixture of caprylic-capric triglycerides sold under the trade name "Miglyol 812" by Dynamit Nobel | 4.0 g |
| S—carboxy methyl cysteine | 3.0 g |
| Triethanolamine, 99% | 2.5 g |
| 4-(4,4-dimethyl-3,4-dihydro-6-benzopyranyl) carbonyl benzoic acid - Example II | 0.10 g |
| Water, sufficient amount for | 100 g |

In this Example, the active compound according to Example II can be replaced by the same amount of 6-[4,4-dimethyl-3,4,-dihydro-6-benzopyranyl) hydroxymethyl]-2-naphthalene carboxylic acid-EXAMPLE XV.

EXAMPLE 5—

Anti-seborrhea cream

| | |
|---|---|
| Polyoxyethylenated stearate (40 moles ethylene oxide), sold under the trade name "Myrij 52" by Atlas | 4.0 g |

-continued

| | |
|---|---|
| Mixture of lauryl esters of sorbitol and sorbitan, polyoxyethylenated with 20 moles of ethylene oxide, sold under the trade name "Tween 20" by Atlas | 1.8 g |
| Mixture of mono- and distearate of glycerol, sold under the trade name "GELEOL" by Gattefosse | 4.2 g |
| Propylene glycol | 10.0 g |
| Buthylhydroxy anisole | 0.01 g |
| Buthylhydroxytoluene | 0.02 g |
| Cetyl-stearyl alcohol | 6.2 g |
| Preservatives, sufficient amount | |
| Perhydrosqualene | 18.0 g |
| Mixture of caprylic-capric triglycerides sold under the trade name "Miglyol 812" by Dynamit Nobel | 4.0 g |
| 5-amino-5-carboxy-3-thia pentanoate of 2-benzylthio ethylammonium N—ethyl-6-(4,4-dimethyl-3,4-dihydro-6-benzothiopyranyl) carbonyl-2-naphthalene carboxamide - Example VIII | 3.0 g |
| Water, sufficient amount for | 100 g |

EXAMPLE 6—

Hair lotion

| | |
|---|---|
| Propylene glycol | 20.0 g |
| Ethanol | 34.87 g |
| Polyethylene glycol, molecular mass 400 | 40.0 g |
| Water | 4.0 g |
| Butyl hydroxy anisole | 0.01 g |
| Buthylhydroxy toluene | 0.02 g |
| 6-(4,4-dimethyl-3,4-dihydro-6-benzopyranyl) carbonyl-2-naphthalene carboxylic acid - Example XII | 0.010 g |
| Minoxidil | 1.0 g |

EXAMPLE 7—

Anti-acne gel

| | |
|---|---|
| trans 4-[(4,4-dimethyl-3,4-dihydro-6-benzothiopyranyl) hydroxymethyl]α-methyl cinnamic acid - Example XIV | 0.20 g |
| Isopropyl alcohol | 40.0 g |
| Polymer of acrylic acid, sold under the trade name "Carbopol 940" by Goodrich Chemical Co. | 1.0 g |
| Triethanolamine, 99% | 0.6 g |
| Buthyl hydroxy anisole | 0.01 g |
| Buthylhydroxy toluene | 0.02 g |
| Tioxolane | 0.5 g |
| Propylene glycol | 8.0 g |
| Purified water, sufficient amount for | 100 g |

EXAMPLE 8—

Anti-acne gel

| | |
|---|---|
| 1-(4,4-dimethyl-3,4-dihydro-6-benzopyranyl)-1-(6-carboxy-2-naphthyl) methane | 0.05 g |

-continued

| | |
|---|---|
| Hydroxypropyl cellulose, sold under the trade name "KLUCEL HF" by Hercules | 2.00 g |
| Water/ethanol (20:80), sufficient amount for | 100.00 g |

What is claimed is:

1. An aromatic benzopyranyl or benzothiopyranyl compound having the formula (II)

wherein n is 0 or 1, $$-O-, -S- \text{ or } -S\underset{O}{\overset{O}{\diagup\diagdown}}$$

R' and R" taken together form an oxo radical or R' represents hydroxyl and R" represents hydrogen, $R_8$ represents $$-OR_9 \text{ or } -N\begin{array}{c}r'\\r''\end{array},$$

$R_9$ represents hydrogen or lower alkyl, r" represents hydrogen and r"represents lower alkyl or mono or poly-hydroxyalkyl.

2. The compound of claim 1 wherein n=1.

3. An aromatic benzopyranyl or benzothiopyranyl compound having the formula (III)

wherein

X represents —O— or —S—, $R_1$ and $R_2$ taken together form an oxo radical or R' represents hydrogen or hydroxy and R" represents hydrogen, $R_1$ and $R_2$ each represent (i) methyl, in which case $R_3$ and $R_4$ represent hydrogen or (ii) hydrogen, in which case $R_3$ and $R_4$ represent methyl, $R_8$ represents hydrogen, $$-OR_9 \text{ or } -N\begin{array}{c}r'\\r''\end{array},$$

$R^9$ represents hydrogen or lower alkyl, r' represents hydrogen and r" represents lower alkyl or mono- or poly hydroxyalkyl.

4. The compound of claim 3 wherein $R_1$ and $R_2$ each represent methyl and $R_3$ and $R_4$ represent hydrogen.

5. An aromatic benzopyranyl or benzothiopyranyl compound selected from the group consisting of 4-(4,4-dimethyl-3,4-dihydro-6-benzopyranyl) carbonyl methyl benzoate, 4-(4,4-dimethyl-3,4-dihydro-6-benzopyranyl) carbonyl benzoic acid, N-ethyl-4-(4,4-dimethyl-3,4-dihydro-6-benzopyranyl) carbonyl benzamide, 4-(4,4-dimethyl-3,4-dihydro-6-benzothiopyranyl) carbonyl methyl benzoate, 4-(4,4-dimethyl-3,4-dihydro-6-benzothiopyranyl) carbonyl benzoic acid, 4-(4,4-dimethyl-3,4-dihydro-6-benzothiopyranyl) carbonyl 2-methyl naphthalene carboxylate, 6-(4,4-dimethyl-3,4-dihydro-6-benzothiopyranyl) carbonyl 2-naphthalene carboxylic acid, N-ethyl 6-(4,4-dimethyl-3,4-dihydro-6-benzothiopyranyl) carbonyl 2-naphthalene carboxamide, 6-(2,2-dimethyl-3,4-dihydro-6-benzopyranyl) carbonyl 2-methyl naphthalene carboxylate, 6-(4,4-dimethyl-3,4-dihydro-6-benzopyranyl) carbonyl 2-methyl naphthalene carboxylate, 6-(2,2-dimethyl-3,4-dihydro-6-benzopyranyl) carbonyl 2-naphthalene carboxylic acid, 6-(4,4-dimethyl-3,4-dihydro-6-benopyranyl) carbonyl 2-naphthalene carboxylic acid, N-ethyl 6-(4,4-dimethyl-3,4-dihydro-6-benzopyranyl) carbonyl 2-naphthalene carboxamide, N-ethyl 6-(4,4-dimethyl-3,4-dihydro-6-benzopyranyl) hydroxymethyl 2-naphthalene carboxamide, 6-(4,4-dimethyl-3,4-dihydro-6-benzopyranyl) hydroxymethyl 2-naphthalene carbinol, 6-(4,4-dimethyl-3,4-dihydro-6-benzopyranyl) carbonyl 2-formyl naphthalene, trans 4-(4,4-dimethyl-3,4,-dihydro-6-benzopyranyl) carbonyl ethyl α-methyl cinnamate, trans 4-(4,4-dimethyl-3,4-dihydro-6-benzopyranyl) carbonyl αmethyl cinnamic acid, N-ethyl trans 4-(4,4-dimethyl-3,4-dihydro-6-benzopyranyl) carbonyl α-methyl cinnamide, trans 4[(4,4dimethyl-3,4-dihydro-6-benzothiopyranyl) hydroxymethyl]-ethyl α-methyl cinnamate, trans 4[(4,4-dimethyl-3,4-dihydro-6-benzothiopyranyl) hydroxymethyl] α-methyl cinnamic acid, trans 4-(4,4-dimethyl-3,4-dihydro-6-benzothiopyranyl) carbonyl α-methyl cinnamic acid, 6[(4,4-dimethyl-3,4dihydro-6-benzopyranyl] hydroxymethyl]2-naphthalene carboxylic acid, 4-(4,4-dimethyl-3,4-dihydro-6-benzothiopyranyl) hydroxymethyl methylbenzoate, 4-[(4,4-dimethyl-3,4-dihydro-6-benzothiopyranyl) hydroxymethyl] benzoic acid and 1-(4,4-dimethyl-3,4-dihydro-6-benzopyranyl)-1-(6-carboxy-2-naphthyl) methane.

6. A pharmaceutical composition useful in the treatment of dermatologic diseases, rheumatoid psoriasis and corneopathies comprising in a pharmaceutically acceptable vehicle, suitable for enteral, parenteral, topical or ocular administration, from 0.0001 to 5 percent by weight of the compound of claim 1 based on the total weight of said composition.

7. A cosmetic composition for body and hair hygiene comprising in a cosmetically acceptable vehicle from 0.0001 to 2 percent by weight of the compound of claim 1 based on the total weight of said composition.

8. A pharmaceutical composition useful in the treatment of dermatologic diseases, rheumatoid psoriasis and corneopathies comprising in a phrmaceutically acceptable vehicle, suitable for enteral, parenteral, topical or ocular administration, from 0.0001 to 5 percent by weight of the compound of claim 3 based on the total weight of said composition.

9. A cosmetic composition for body and hair hygiene comprising in a cosmetically acceptable vehicle from 0.0001 to 2 percent by weight of the compound of claim 3 based on the total weight of said composition.

10. A pharmaceutical composition useful in the treatment of dermatologic diseases, rheumatoid psoriasis and corneopathies comprising in a pharmaceutically acceptable vehicle, suitable for enteral, parenteral, topical or ocular administration, from 0.001 to 5 percent by weight of the compound of claim 5 based on the total weight of said composition.

11. A cosmetic composition for body and hair hygiene comprising in a cosmetically acceptable vehicle from 0.0001 to 2 percent by weight of the compound of claim 5 based on the total weight of said composition.

* * * * *